United States Patent [19]

Fukuto et al.

[11] 4,410,518
[45] Oct. 18, 1983

[54] N-PHOSPHINOAMINOSULFINYLCARBAMATE ESTERS AND THEIR USE AS INSECTICIDES

[75] Inventors: Tetsuo R. Fukuto; Hiroki Ohta, both of Riverside, Calif.

[73] Assignee: Regents of the University of California, Berkeley, Calif.

[21] Appl. No.: 360,719

[22] Filed: Mar. 22, 1982

[51] Int. Cl.$^3$ .................... A01N 57/04; A01N 57/08; C07F 9/24
[52] U.S. Cl. ................................. 424/202; 424/203; 424/209; 424/211; 549/6; 549/220; 260/453.3; 260/937; 260/938
[58] Field of Search ............... 549/6, 220; 260/453.3, 260/937, 938, 984; 424/202, 203, 209, 211

[56] References Cited

U.S. PATENT DOCUMENTS

| | | | |
|---|---|---|---|
| 4,261,897 | 4/1981 | Fahmy et al. | 549/438 |
| 4,279,897 | 7/1981 | Fahmy et al. | 260/938 |
| 4,297,285 | 10/1981 | Nelson | 549/220 |

OTHER PUBLICATIONS

Kharasch, Org. Sulfur Compounds, vol. 1 Pergamon Press (1961) p. 499.

Primary Examiner—Henry R. Jiles
Assistant Examiner—Bernard Dentz
Attorney, Agent, or Firm—Nilsson, Robbins, Dalgarn, Berliner, Carson & Wurst

[57] ABSTRACT

A novel class of chemical compounds useful as pesticides consists of N-phosphinoaminosulfinylcarbamate esters. The preparation of these compounds and their formulation to control insects are exemplified.

23 Claims, No Drawings

N-PHOSPHINOAMINOSULFINYLCARBAMATE ESTERS AND THEIR USE AS INSECTICIDES

FIELD OF THE INVENTION

This invention relates to the general field of pesticides, and is particularly concerned with the production of insecticides for the control of both household insects and crop insects.

BACKGROUND AND SUMMARY OF THE INVENTION

Various types of carbamate and carbamate ester insecticides have previously been described. For example, U.S. Pat. No. 3,997,549 to Fukuto and Black discloses N-aryl-sulfenylated derivatives of benzofuranyl methylcarbamates as effective pesticides. U.S. Pat. No. 4,006,231 to Black and Fukuto discloses N-aminosulfenylated derivatives of carbofuran as effective pesticides; U.S. Pat. No. 3,843,689 to Brown discloses production of N-methyl- or N-phenyldithiocarbamates produced from N-chlorothiocarbamates as insecticides; and U.S. Pat. No. 4,261,897 to Fahmy and Fukuto discloses production of N-chlorosulfinylcarbamate esters produced from carbamates as useful intermediates in the preparation of pesticides. In addition, U.S. Pat. Nos. 4,262,015 and 4,263,318 to Fahmy and Fukuto disclose N-alkylthio- and N-arylthiosulfinylcarbamate esters, and N-alkoxy- and N-aryloxysulfinylcarbamate esters, respectively, as insecticides. Further, amidothioate ester insecticides are described in U.S. Pat. No. 4,279,897 to Fahmy and Fukuto, and thiomethyl carbamate pesticides are disclosed in U.S. Pat. No. 4,081,536 to Nelson. U.S. Pat. No. 4,006,231 to Black and Fukuto discloses N-aminosulfenylated derivatives of carbofuran and U.S. Pat. No. 3,843,689 to Brown and Kohn describes the production of N-chlorothio-carbamates useful in the production of pesticides.

In accordance with the present invention, a novel class of carbamate compounds is provided, the compounds being effective as pesticides. More particularly, the compounds are generally N-phosphinoaminosulfinylcarbamate esters which are useful as insecticides and are prepared by reacting on N-chlorosulfinylcarbamate esters with phosphoramidates or phosphoramidothioates, using a hydrogen chloride acceptor such as pyridine either in the presence or absence of a suitable organic solvent.

The resulting compounds of the invention are highly effective against certain pests and insects, and have substantially reduced mammalian toxicity, e.g., as compared to other potent carbamate insecticides such as carbofuran, described in U.S. Pat. No. 3,474,171. Thus, the invention compounds, while having high toxicity toward certain pests or insects, are relatively safe to mammals.

In the following detailed description, all temperatures are intended as having been expressed in degrees centigrade, unless otherwise indicated by the context of the specification.

DETAILED DESCRIPTION

The sulfinyl carbamate esters of the invention have the formula noted below:

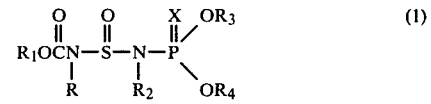

in which
R is alkyl of 1 to 4 carbon atoms;
$R_1$ is a heterocyclic group of the formula

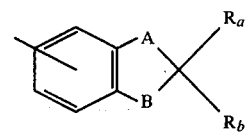

in which $R_a$ and $R_b$ are hydrogen or alkyl of 1 to 4 carbon atoms, A and B are each oxygen or one of A and B is methylene and the other is oxygen or sulfur, attached at the 4 or 7 position, for example, 2,3-dihydro-2,2-dimethyl-7-benzofuranyl or 2,2-dimethyl-1,3-benzodioxol-4-yl; or an imino group of the formula

wherein $R_c$ is hydrogen, a dialkylaminocarbonyl or alkyl of 1 to 4 carbon atoms and $R_d$ is alkylthio or alkylthioalkyl, in which the alkyl groups are the same or different and have 1 to 4 carbon atoms;

$R_2$ is alkyl of 1 to 12 carbon atoms, or cycloalkyl of 3 to 6 carbon atoms;

$R_3$ and $R_4$, the same or different, are alkyl of 1 to 6 carbon atoms, or together can constitute the carbons necessary to complete a 5 to 6 membered ring system which can optionally be substituted by 1 or 2 methyl groups, for example,

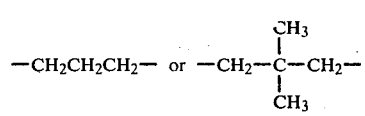

and X is oxygen or sulfur.

Preferred carbamates of the invention are those of formula (1) above, where R is a methyl; $R_1$ is 2,3-dihydro-2,2-dimethyl-7-benzofuranyl, or a group containing an imino group of the formula (2), such groups can be, for example, the following:

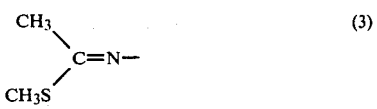

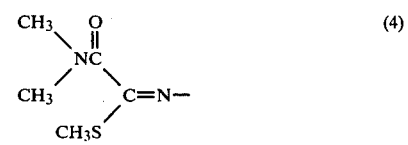

$R_2$ is alkyl of 1 to 6 carbon atoms; $R_3$ and $R_4$, the same or different, are alkyl of 1 to 3 carbon atoms, or together can constitute the group which is

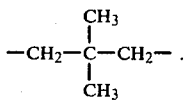

The compound of this invention can be prepared by the reaction of N-chlorosulfinylcarbamate esters with phosphoramidates or phosphoramidothioates as described in the following equation (5);

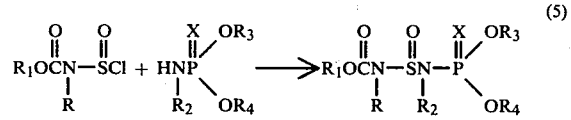

(5)

wherein R, $R_1$, $R_2$, $R_3$, $R_4$, and X are the same as those described in formula (1).

The N-chlorosulfinylcarbamate ester starting material is obtained by the reaction of the corresponding carbamate ester with thionyl chloride preferably using pyridine as the hydrogen chloride acceptor in the presence or in the absence of inert organic solvent; for example, dichloromethane or tetrahydrofuran. These intermediates are described in U.S. Pat. No. 4,261,897 to Fahmy and Fukuto.

Without isolation, the N-chlorosulfinylcarbamate ester intermediate can react in situ with an equimolar amount of phosphoramidates or phosphoramidothioates according to equation (5). However, if desired, the N-chlorosulfinylcarbamate ester starting material can be initially isolated as an intermediate, and such compound then reacted with the appropriate phosphorus compound according to the equation (5).

In the equation (5) above, various bases can be used as acid acceptors. These include pyridine, alkylpyridines, quinolines, and similar heterocyclic bases. The preferred base is pyridine, which serves as a solvent and acid acceptor.

The reaction temperature for (5) can range from $-30°$ to $50°$ C. according to the reactivity of the phosphorus compound.

The following examples illustrate preparation of the carbamates of this invention.

EXAMPLE 1

Synthesis of 2,3-dihydro-2,2-dimethyl-7-benzofuranyl[[(diethoxyphosphinothioyl)methylamino]sulfinyl]methylcarbamate To a stirred solution of 2,3-dihydro-2,2-dimethyl-7-benzofuranyl methylcarbamate (2.21 g, 0.01 mole) in dry pyridine (8 ml) was added at one time thionyl chloride (1.19 g, 0.01 mole) at $-30°$ C. The mixture was allowed to come to room temperature, and then stirred for 15 minutes. The mixture was cooled to 0° and O,O-diethyl methylphosphoramidothioate (1.83 g, 0.01 mole) was added. the mixture was allowed to come to room temperature for 1 hour, poured into ice-water and extracted with benzene. The benzene solution was washed with water 4 times and then dried over anhydrous sodium sulfate. The benzene was removed under reduced pressure to give crude carbamate compound of the formula below.

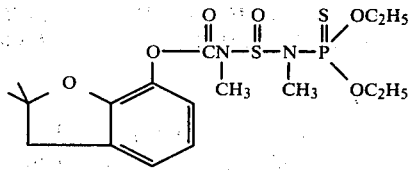

The product was purified by silica gel chromatography using benzene-acetonitrile (30:1) as an eluent, to yield 2.5 g product. The NMR spectrum (CDCl$_3$-TMS) of the compound showed the following absorptions:

| δ | |
|---|---|
| 1.25 | (6H, t, OCH$_2$CH$_3$) |
| 1.45 | (6H, s, gem, di-CH$_3$) |
| 2.78 | (3H, d, —NCH$_3$) |
| 2.97 | (5H, s, benzylic CH$_2$, and CONCH$_3$) |
| 3.87~4.17 | (4H, m, —OCH$_2$CH$_3$) |
| 6.57~6.93 | (3H, m, aromatic) |

EXAMPLE 2

Synthesis of 2,3-dihydro-2,2-dimethyl-7-benzofuranyl[[(diethoxyphosphinothioyl)propylamino]sulfinyl]methylcarbamate 2-3-Dihydro-2,2-dimethyl-7-benzofuranyl[[(diethoxyphosphinothioyl)-propylamino]sulfinyl]methylcarbamate was prepared by the procedure employed in Example 1, by reacting 2,3-dihydro-2,2-dimethyl-7-benzofuranyl methylcarbamate (2.21 g, 0.01 mole), thionyl chloride (1.19 g, 0.01 mole), and O,O-diethyl propylphosphoramidothioate (2.11 g, 0.01 mole) in pyridine (8 ml). Column chromatography afforded 2.9 g of an oil of the formula below.

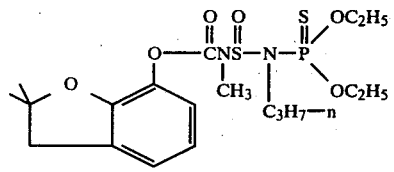

The NMR spectrum (CDCl$_3$-TMS) of the compound showed the following absorptions:

| δ | |
|---|---|
| 0.90 | (3H, t, —CH$_2$CH$_2$CH$_3$) |
| 1.22, 1.27 | (6H, two t, —OCH$_2$CH$_3$) |
| 1.43 | (6H, s, gem-diCH$_3$) |
| 1.63 | (2H, sextet, —CH$_2$CH$_2$CH$_3$) |
| 2.97 | (5H, s, benzylic CH$_2$ and CONCH$_3$) |
| 3.00~3.40 | (2H, m, —CH$_2$CH$_2$CH$_3$) |
| 3.86~4.17 | (4H, m, OCH$_2$CH$_3$) |
| 6.57~6.90 | (3H, m, aromatic) |

EXAMPLE 3

Synthesis of 2,3-dihydro-2,2-dimethyl-7-benzofuranyl[[(diethoxyphosphinothioyl)hexylamino]sulfinyl]methylcarbamate 2,3-Dihydro-2,2-dimethyl-7-benzofuranyl[[(diethoxyphosphinothioyl)hexylamino]sulfinyl]methylcarbamate was prepared by the procedure employed in Example 1, by reacting 2,3-dihydro-2,2-dimethyl 7-benzofuranyl methylcarbamate (2.21 g, 0.01 mole), thionyl chloride (1.19 g, 0.01 mole), and O,O-diethyl n-hexyl-phosphoramidothioate (2.52 g, 0.01 mole), in pyridine (8 ml). Column chromatography afforded 3.3 g of an oil of the formula below.

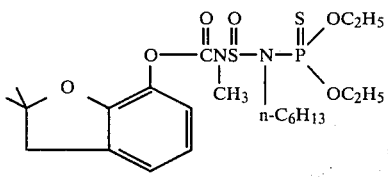

The NMR spectrum (CDCl₃-TMS) of the compound showed the following absorptions:

| δ | |
|---|---|
| 0.87 | (3H, t, CH₃ of hexyl chain) |
| 1.13~1.33 | (14H, m, OCH₂2CH₃ and hexyl) |
| 1.46 | (6H, s, gem-diCH₃) |
| 2.97 | (5H, s, benzylic CH₂, and NCH₃) |
| 3.10~3.47 | (2H, m, NCH₂) |
| 3.83~4.17 | (4H, m, OCH₂CH₃) |
| 6.56~6.93 | (3H, m, aromatic) |

EXAMPLE 4

Synthesis of 2,3-dihydro-2,2-dimethyl-7-benzofuranyl[[(diethoxyphosphinothioyl)dodecylamino]sulfinyl]methylcarbamate 2,3-Dihydro-2,2-dimethyl-7-benzofuranyl[[(diethoxyphosphinothioyl)dodecylamino]sulfinyl]methylcarbamate was prepared by the procedure employed in Example 1, by reacting 2,3-dihydro-2,2-dimethyl-7-benzofuranyl methylcarbamate (2.21 g, 0.01 mole), thionyl chloride (1.19 g, 0.01 mole), and O,O-diethyl dodecylphosphoramidothioate (3.37 g, 0.01 mole) in pyridine (8 ml). Column chromatography afforded 2.4 g of an oil of the formula

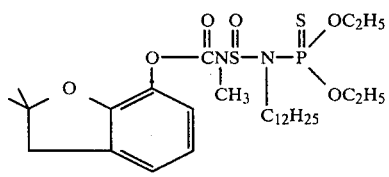

The NMR spectrum (CDCl₃ TMS) of the compound showed the following absorptions:

| δ | |
|---|---|
| 0.86 | (3H, t) |
| 1.14~1.33 | (26H, m, OCH₂CH₃, and alkyl chain) |
| 1.43 | (6H, s, gem-diCH₃) |
| 2.97 | (5H, s, benzylic CH₂, and CONCH₃) |
| 3.29 | (2H, quintet NCH₂) |
| 4.03~4.20 | (4H, m, OCH₂CH₃) |
| 6.58~6.93 | (3H, m, aromatic) |

EXAMPLE 5

Synthesis of 2,3-dihydro-2,2-dimethyl-7-benzofuranyl[[(5-dimethyl-2-thioxo-1,3,2-dioxaphosphorinan-2-yl)methylamino]sulfinyl]methylcarbamate 2,3-Dihydro-2,2-dimethyl-7-benzofuranyl[[(5,5-dimethyl-2-thioxo-1,3,2-dioxaphosphorinan-2-yl)methylamino]sulfinyl]methylcarbamate was prepared by the procedure employed in Example 1, by reacting 2,3-dihydro-2,2-dimethyl-7-benzofuranyl methylcarbamate (1.19 g, 0.01 mole), and 5,5-dimethyl-2-methylamino-2-thioxo-1,3,2-dioxaphosphorinan (1.95 g, 0.01 mole) in pyridine (8 ml). Column chromatography and subsequent recrystallization from hexane-benzene afforded 2.70 g of needles of the formula below, mp 91~93°.

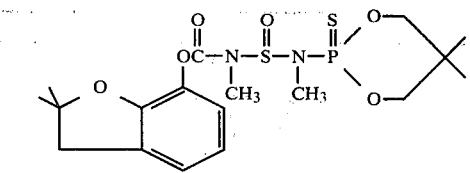

Analysis calculated for C₁₈H₂₇O₆N₂S₂P; carbon, 46.74%, hydrogen, 5.88%. Found: carbon, 46.87%, hydrogen, 6.07%.

The NMR spectrum (CDCl₃-TMS) of the compound showed the following absorptions:

| δ | |
|---|---|
| 0.93 | (3H, s, —C(CH₃)—) with CH₃ |
| 1.10 | (3H, s, —C(CH₃)—) with CH₃ |
| 1.44 | (6H, s, gem-diCH₃) |
| 2.97 | (3H, d, NCH₃) |
| 3.03 | (2H, s, benzylic CH₂) |
| 3.05 | (3H, s, CONCH₃) |
| 3.57–4.35 | (4H, m, O—CH₂ / O—CH₂ ring) |
| 6.63–7.00 | (3H, m, aromatic) |

EXAMPLE 6

Synthesis of 2,3-dihydro-2,2-dimethyl-7-benzofuranyl[[(5,5-dimethyl-2-thioxo-1,3,2-dioxaphosphorinan-2-yl)hexylamino]sulfinyl]methylcarbamate 2,3-Dihydro-2,2-dimethyl-7-benzofuranyl[[(5,5-dimethyl-2-thioxo-1,3,2-dioxaphosphorinan-2-yl)hexylamino]sulfinyl]methylcarbamate was prepared by the procedure employed in Example 1, by reacting 2,3-dihydro-2,2-dimethyl-7-benzofuranyl methylcarbamate (2.21 g, 0.01 mole), thionyl chloride (1.19 g, 0.01 mol), and 5,5-dimethyl-2-hexylamino-2-thioxo-1,3,2-dioxaphosphorinan (2.65 g, 0.01 mole) in pyridine (8 ml). Column chromatography afforded 3.1 g of an oil of the formula below.

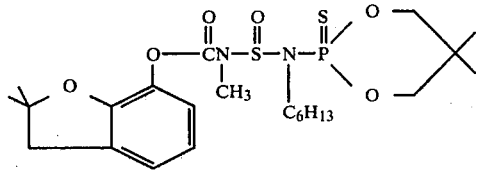

The NMR spectrum (CDCl$_3$-TMS) of the compound showed the following absorptions:

| δ | |
|---|---|
| 0.83 | (3H, s, —C(CH$_3$)$_2$—) |
| 0.87 | (3H, t,) |
| 1.10 | (3H, s, —C(CH$_3$)$_2$—) |
| 1.20~1.70 | (8H, m, alkyl) |
| 1.43 | (6H, s, gem-diCH$_3$) |
| 2.95 | (2H, s, benzylic CH$_2$) |
| 2.97 | (3H, s, NCH$_3$) |
| 3.23-4.33 | (6H, m, O—CH$_2$\\ \\>< /O—CH$_2$, and NCH$_2$) |
| 6.57-6.93 | (3H, m, aromatic) |

EXAMPLE 7

Synthesis of 2,3-dihydro-2,2-dimethyl-7-benzofuranyl[[(diethoxyphosphinyl)methylamino]sulfinyl]methylcarbamate 2,3-Dihydro-2,2-dimethyl-7-benzofuranyl[[(diethoxyphosphinyl)methylamino]sulfinyl]methylcarbamate was prepared by the procedure employed in Example 1, by reacting 2,3-dihydro-2,2-dimethyl-7-benzofuranyl methylcarbamate (2.21 g, 0.01 mol), thionyl chloride (1.19 g, 0.01 mole), and O,O-diethyl methylphosphoramidate (1.67 g, 0.01 mole) in pyridine (8 ml). Column chromatography afforded 3.0 g of an oil of the formula below.

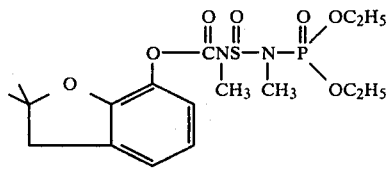

The NMR Spectrum (CDCl$_3$-TMS) of the compound showed the following absorptions:

| δ | |
|---|---|
| 1.27 | (6H, t, OCH$_2$CH$_3$) |
| 1.46 | (6H, s, gem-diCH$_3$) |
| 2.75 | (3H, d, NCH$_3$) |
| 2.97 | (2H, s, benzylic CH$_2$) |
| 2.98 | (3H, s, CONCH$_3$) |
| 4.00 | (4H, quintet OCH$_2$CH$_3$) |
| 6.60~6.97 | (3H, m, aromatic) |

EXAMPLE 8

Synthesis of 2,3-dihydro-2,2-dimethyl-7-benzofuranyl[[(diethoxyphosphinyl)propylamino]sulfinyl]methylcarbamate 2,3-Dihydro-2,2-dimethyl-7-benzofuranyl[[(diethoxyphosphinyl)propylamino]sulfinyl]methylcarbamate was prepared by the procedure employed in Example 1, by reacting 2,3-dihydro-2,2-dimethyl-7-benzofuranyl methylcarbamate (2.21 g, 0.01 mole), thionyl chloride (1.19 g, 0.01 mole), and O,O-diethyl propylphosphoramidate (1.95 g, 0.01 mole) in pyridine. Column chromatography afforded 2.2 g of an oil of the formula below.

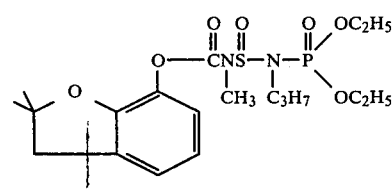

The NMR spectrum (CDCl$_3$-TMS) of the compound showed the following absorptions:

| δ | |
|---|---|
| 0.92 | (3H, t, CH$_2$CH$_2$CH$_3$) |
| 1.24 | (3H, t, OCH$_2$CH$_3$) |
| 1.28 | (3H, t, OCH$_2$CH$_3$) |
| 1.43 | (6H, s, gem-diCH$_3$) |
| 1.50~1.80 | (2H, m, —CH$_2$CH$_2$CH$_3$) |
| 2.97 | (5H, s, benzylic CH$_2$, and NCH$_3$) |
| 3.00~3.30 | (2H, m, —CH$_2$CH$_2$CH$_3$) |
| 4.00 | (4H, quintet, OCH$_2$CH$_3$) |
| 6.56~6.93 | (3H, m, aromatic) |

EXAMPLE 9

Synthesis of methyl N-[[[[[(dimethoxyphosphinothioyl)methylamino]sulfinyl]methylamino]carbonyl]oxy]ethanimidothioate To a stirred solution of methyl N-[[(methylamino)carbonyl]oxy]ethaniminidothioate (2.43 g, 0.015 mole) in dry pyridine 10 ml was added at one time thionyl chloride (1.79 g, 0.015 mole) at −30°. The mixture was allowed to come to room temperature and then stirred for 15 minutes. The mixture was cooled to 0° and O,O-dimethyl methylphosphoramidothioate (2.33 g, 0.015 mole) was added. The mixture was allowed to stand at room temperature for 1 hour and poured into ice water. The resulting precipitate was collected and recrystallized from chloroform-hexane, to yield 3.20 g of colorless prisms of the formula below, mp 89~91°.

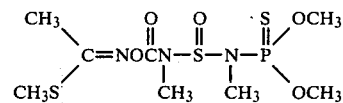

Analysis calculated for $C_8H_{18}N_3O_5S_3P$; Carbon, 26.44%; Hydrogen, 4.99%. Found: carbon 26.12%, hydrogen, 4.86%.

The NMR spectrum (CDCl$_3$-TMS) of the compound showed the following absorptions:

| δ | |
|---|---|
| 2.27 | (3H, s, CH$_3$) |
| 2.38 | (3H, s, SCH$_3$) |
| 2.78 | (3H, d, NCH$_3$) |
| 2.97 | (3H, s, CONCH$_3$) |
| 3.72 | (6H, d, OCH$_3$) |

EXAMPLE 10

Synthesis of methyl N-[[[[[(dimethoxyphosphinothioyl)ethylamino]sulfinyl]methylamino]carbonyl]oxy]ethanimidothioate Methyl N-[[[[[(dimethoxyphosphinothioyl)ethylamino]sulfinyl]methylamino]carbonyl]oxy]ethanimidothioate was prepared by the procedure employed in Example 9, by reacting methyl N-[[(methylamino)carbonyl]oxy]ethanimidothioate (2.43 g, 0.015 mole), thionyl chloride (1.79 g, 0.015 mole), and O,O-dimethylethylphosphoramidothioate (2.57 g, 0.015 mole) in pyridine (10 ml). Recrystallization from chloroformhexane afforded 2.20 g of colorless prisms of the formula below, mp 66~68°.

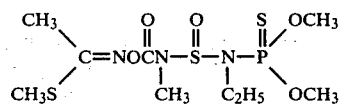

Analysis calculated for $C_9H_{20}N_3O_5S_3P$; carbon, 28.64%; hydrogen, 5.34%; Found: carbon, 29.02%; hydrogen, 5.67%.

The NMR spectrum (CDCl$_3$-TMS) of the compound showed the following absorptions:

| δ | |
|---|---|
| 1.20 | (3H, t, NCH$_2$CH$_3$) |
| 2.25 | (3H, s, CH$_3$) |
| 2.37 | (3H, s, SCH$_3$) |
| 2.93 | (3H, s, NCH$_3$) |
| 3.23~3.70 | (2H, sextet, NCH$_2$CH$_3$) |
| 3.72 | (6H, d, OCH$_3$) |

EXAMPLE 11

Synthesis of methyl N-[[[[[(diethoxyphosphinothioyl)methylamino]sulfinyl]methylamino]carbonyl]oxy]ethanimidothioate Methyl N-[[[[[(diethoxyphosphinothioyl)methylamino]sulfinyl]methylamino]carbonyl]oxy]ethanimidothioate was prepared by the procedure employed in Example 9, by reacting methyl N-[[(methylamino)carbonyl]oxy]ethanimidothioate (2.43 g, 0.015 mole), thionyl chloride (1.79 g, 0.015 mole), and O,O-diethyl methylphosphoramidothioate (2.75 g, 0.015 mole) in pyridine (10 ml). Recrystallization from chloroformhexane afforded 2.75 g of colorless prisms of the formula below, mp 78~78.5°.

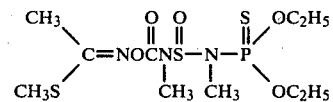

Analysis calculated for $C_{10}H_{22}N_3O_5S_3P$; carbon, 30.68%, hydrogen, 5.66%. Found: Carbon, 30.92%; hydrogen, 5.82%.

The NMR spectrum (CDCl$_3$-TMS) of the compound showed the following absorptions:

| δ | |
|---|---|
| 1.30 | (6H, t, OCH$_2$CH$_3$) |
| 2.26 | (3H, s, CH$_3$) |
| 2.37 | (3H, s, SCH$_3$) |
| 2.77 | (3H, d, NCH$_3$) |
| 2.93 | (3H, s, CONCH$_3$) |
| 3.86~4.25 | (4H, m, OCH$_2$CH$_3$) |

EXAMPLE 12

Synthesis of methyl N-[[[[[(diethoxyphosphinothioyl)ethylamino]sulfinyl]methylamino]carbonyl]oxy]ethanimidothioate Methyl N-[[[[[(diethoxyphosphinothioyl)ethylamino]sulfinyl]methylamino]carbonyl]oxy]ethanimidothioate was prepared by the procedure employed in Example 9, by reacting methyl N-[[(methylamino)carbonyl]oxy]ethanimidothioate (2.43 g, 0.015 mole), thionyl chloride (1.79 g, 0.015 mole), and O,O-diethyl ethylphosphoramidothioate (2.96 g, 0.015 mole) in pyridine (10 ml). Recrystallization from chloroform-hexane afforded 2.95 g of colorless prisms of the formula below, mp 67~68°.

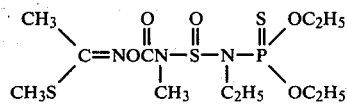

Analysis calculated for $C_{11}H_{24}N_3O_5S_3P$; carbon, 32.58% hydrogen, 5.97%. Found: carbon, 33.25%; hydrogen, 6.00%.

The NMR spectrum (CDCl$_3$-TMS) of the compound showed the following absorptions:

| δ | |
|---|---|
| 1.20 | (3H, t, CH$_2$CH$_3$) |
| 1.30 | (6H, t, OCH$_2$CH$_3$) |
| 2.23 | (3H, s, CH$_3$) |
| 2.35 | (3H, s, SCH$_3$) |
| 2.92 | (3H, s, NCH$_3$) |
| 3.43 | (2H, sextet, CH$_2$CH$_3$) |
| 4.07 | (4H, quintet, OCH$_2$CH$_3$) |

EXAMPLE 13

Synthesis of methyl N-[[[[[(diethoxyphosphinothioyl)propylamino]sulfinyl]methylamino]carbonyl]oxy]ethanimidothioate Methyl N-[[[[[(diethoxyphosphinothioyl)propylamino]sulfinyl]methylamino]carbonyl]oxy]ethanimidothioate was prepared by the procedure employed in Example 9, by reacting methyl N-[[(methylamino)carbonyl]oxy]ethanimidothioate (2.43 g, 0.015 mole), thionyl chloride (1.79 g, 0.015 mole), and O,O-diethyl propylphosphoramidothioate (3.17 g, 0.015 mole) in pyridine (10 ml). Recrystallization from benzene-hexane afforded 3.87 g of colorless prisms of the formula below, mp 58~59°.

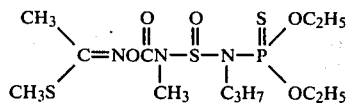

Analysis calculated for $C_{12}H_{26}N_3O_5S_3P$; carbon, 34.35%, hydrogen, 6.25%. Found: carbon, 34.63%; hydrogen, 6.34%.

The NMR spectrum (CDCl$_3$-TMS) of the compound showed the following absorptions:

| δ | |
|---|---|
| 0.88 | (3H, t, —CH$_2$CH$_2$CH$_3$) |
| 1.30 | (6H, t, —OCH$_2$CH$_3$) |
| 1.30~2.00 | (2H, m, —CH$_2$CH$_2$CH$_3$) |
| 2.27 | (3H, s, CH$_3$) |
| 2.37 | (3H, s, SCH$_3$) |
| 2.92 | (3H, s, CONCH$_3$) |
| 3.10~3.50 | (2H, m, CH$_2$CH$_2$CH$_3$) |
| 3.90~4.23 | (4H, m, OCH$_2$CH$_3$) |

EXAMPLE 14

Synthesis of methyl N-[[[[[(diethoxyphosphinothioyl)isopropylamino]sulfinyl]methylamino]carbonyl]oxy]ethanimidothioate Methyl N-[[[[[(diethoxyphosphinothioyl)isopropylamino]sulfinyl]methylamino]carbonyl]oxy]ethanimidothioate was prepared by the procedure employed in Example 9, by reacting methyl N-[[(methylamino)carbonyl]oxy]ethanimidothioate (2.43 g, 0.015 mole), thionyl chloride (1.79 g, 0.015 mole), and O,O-diethyl isopropylphosphoramidothioate (3.17 g, 0.015 mole) in pyridine (10 ml). Recrystallization from cyclohexane afforded 1.73 g of colorless prisms of the formula below, mp 53~54°.

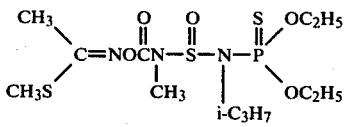

The NMR spectrum (CDCl$_3$-TMS) of the compound showed the following absorptions:

| δ | |
|---|---|
| 1.17~1.45 | (6H, m, OCH$_2$CH$_3$) |
| 1.38 | (6H, d, [CH$_3$]$_2$CH—) |
| 2.21 | (3H, s, CH$_3$) |
| 2.33 | (3H, s, SCH$_3$) |
| 2.87 | (3H, s, CONCH$_3$) |
| 3.82–4.30 | (5H, m, OCH$_2$CH$_3$ and [CH$_3$]$_2$CH) |

EXAMPLE 15

Synthesis of methyl N-[[[[[(diethoxyphosphinothioyl)sec-butylamino]sulfinyl]methylamino]carbonyl]oxy]ethanimidothioate Methyl N-[[[[[(diethoxyphosphinothioyl)sec-butylamino]sulfinyl]methylamino]carbonyl]oxy]ethanimidothioate was prepared by the procedure employed in Example 9, by reacting methyl N-[[(methylamino)carbonyl]oxy]ethanimidothioate (2.43 g, 0.015 mole), thionyl chloride (1.79 g, 0.015 mole), and O,O-diethyl sec-butylphosphoramidothioate (3.38 g, 0.015 mole) in pyridine (10 ml). Recrystallization from benzene-ethyl acetate afforded 2.9 g of the formula below, mp 62~63°.

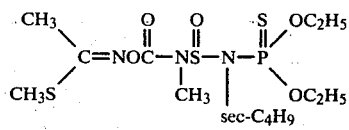

The NMR spectrum (CDCl$_3$-TMS) of the compound showed the following absorptions:

| δ | |
|---|---|
| 0.90 | (3H, t, CH[CH$_3$]CH$_2$CH$_3$) |
| 1.20~1.45 | (12H, m, OCH$_2$CH$_3$, CH[CH$_3$]CH$_2$CH$_3$) |
| 1.50~2.08 | (2H, m, CH[CH$_3$]CH$_2$CH$_3$) |
| 2.27 | (3H, S, CH$_3$) |
| 2.30 | (3H, s, SCH$_3$) |
| 2.90 | (3H, s, NCH$_3$) |
| 3.90–4.30 | (5H, m, OCH$_2$CH$_3$, CH[CH$_3$]CH$_2$CH$_3$) |

EXAMPLE 16

Synthesis of methyl N-[[[[[(diethoxyphosphinothioyl)cyclopentylamino]sulfinyl]methylamino]carbonyl]oxy]ethanimidothioate Methyl N-[[[[[(diethoxyphosphinothioyl)cyclopentylamino]sulfinyl]methylamino]carbonyl]oxy]ethanimidothioate was prepared by the procedure employed in Example 9, by reaching methyl N-[[(methylamino)carbonyl]oxy]ethanimidothioate (2.43 g, 0.015 mole), thionyl chloride (1.79 g, 0.015 mole) and O,O-diethyl cyclopentylphosphoramidothioate (3.56 g, 0.015 mole) in pyridine. Recrystallization from cyclohexane afforded 1.0 g of colorless prisms of the formula below, mp 79~80°.

The NMR spectrum (CDCl$_3$-TMS) of the compound showed the following absorptions:

| δ | |
|---|---|
| 1.28 | (3H, t, OCH$_2$CH$_3$) |
| 1.30 | (3H, t, OCH$_2$CH$_3$) |
| 1.30–2.30 | (8H, m, cyclopentyl) |
| 2.27 | (3H, s, CH$_3$) |
| 2.37 | (3H, s, SCH$_3$) |
| 2.93 | (3H, s, CONCH$_3$) |
| 3.87~4.28 | (5H, m, OCH$_2$CH$_3$, N—CH) |

EXAMPLE 17

Synthesis of methyl N-[[[(diethoxyphosphinothioyl)-hexylamino]sulfinyl]methylamino]carbonyl]oxy]ethanimidothioate Methyl N-[[[[[(diethoxyphosphinothioyl)hexylamino]sulfinyl]methylamino]carbonyl]oxy]ethanimidothioate was prepared by the procedure employed in Example 9, by reacting methyl N-[[(methylamino)carbonyl]oxy]ethanimidothioate (2.43 g, 0.015 mole), thionyl chloride (1.79 g, 0.015 mole) and O,O-diethyl hexylphosphoramidothioate (3.80 g, 0.015 mole) in pyridine (10 ml). Column chromatography afforded 2.9 g of an oil of the formula below.

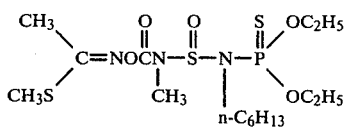

The NMR spectrum (CDCl$_3$-TMS) of the compound showed the following absorptions:

| δ | |
|---|---|
| 0.88 | (3H, t) |
| 1.29 | (3H, t, OCH$_2$CH$_3$) |
| 1.31 | (3H, t, OCH$_2$CH$_3$) |
| 1.15~1.80 | (8H, m, alkyl) |
| 2.24 | (3H, s, CH$_3$) |
| 2.37 | (3H, s, SCH$_3$) |
| 2.87 | (3H, s, CONCH$_3$) |
| 3.27 | (2H, quintet, NCH$_2$) |
| 3.37~4.22 | (4H, m, OCH$_2$CH$_3$) |

EXAMPLE 18

Synthesis of methyl N-[[[[[(diethoxyphosphinothioyl)cyclohexylamino]sulfinyl]methylamino]carbonyl]oxy]ethanimidothioate Methyl N-[[[[[(diethoxyphosphinothioyl)cyclohexylamino]sulfinyl]methylamino]carbonyl]oxy]ethanimidothioate was prepared by the procedure employed in Example 9, by reacting methyl N-[[(methylamino)carbonyl]oxy]ethanimidothioate (2.43 g, 0.015 mole), thionyl chloride (1.79 g, 0.015 mole) and O,O-diethyl cyclohexylphosphoramidothioate (3.77 g, 0.015 mole) in pyridine 10 ml. Recrystallization from chloroform-hexane afforded 2.5 g of colorless prisms of the formula below, mp 72~74°.

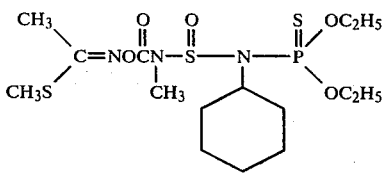

Analysis calculated for C$_{14}$H$_{30}$N$_3$O$_5$S$_3$P; carbon, 39.20%; hydrogen, 6.58%. Found: carbon, 39.52%; hydrogen, 6.56%.

The NMR spectrum (CDCl$_3$-TMS) of the compound showed the following absorptions:

| δ | |
|---|---|
| 1.27 | (3H, t, OCH$_2$CH$_3$) |
| 1.32 | (3H, t, OCH$_2$CH$_3$) |
| 1.10-2.20 | (10H, m, cyclohexyl) |
| 2.27 | (3H, s, CH$_3$) |
| 2.39 | (3H, s, SCH$_3$) |
| 2.93 | (3H, s, CONCH$_3$) |

-continued

| δ | |
|---|---|
| 3.50~4.30 | (5H, m, OCH$_2$CH$_3$, N—CH$\diagup^{}_{\diagdown}$ ) |

EXAMPLE 19

Synthesis of methyl N-[[[[[(5,5-dimethyl-2-thioxo-1,3,2-dioxaphosphorinan-2-yl)(methyl)amino]sulfinyl]methylamino]carbonyl]oxy]ethanimidothioate Methyl N-[[[[[(5,5-dimethyl-2-thioxo-1,3,2-dioxaphosphorinan-2-yl)(methyl)amino]sulfinyl]methylamino]carbonyl]oxy]ethanimidothioate was prepared by the procedure employed in Example 9, by reacting methyl N-[[(methylamino)carbonyl]oxy]ethanimidothioate (2.43 g, 0.015 mole), thionyl chloride (1.79 g, 0.015 mole), and 5,5-dimethyl-2-methylamino-2-thioxo-1,3,2-dioxaphosphorinan (2.93 g, 0.015 mole) in pyridine (10 ml). Recrystallization from chloroform-hexane afforded 3.0 g of needles of the formula below, mp 112~114°.

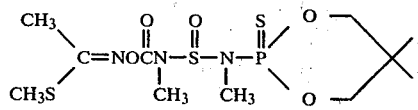

Analysis calculated for C$_{11}$H$_{22}$N$_3$O$_5$S$_3$P; carbon, 32.74%; hydrogen, 5.50%. Found: carbon, 32.91%, hydrogen, 5.24%.

The NMR spectrum (CDCl$_3$-TMS) of the compound showed the following absorptions:

| δ | |
|---|---|
| 1.00 | (3H, s, —C(CH$_3$)$_2$—) with CH$_3$ above and below |
| 1.16 | (3H, s, —C(CH$_3$)$_2$—) with CH$_3$ above and below |
| 2.27 | (3H, s, CH$_3$) |
| 2.37 | (3H, s, SCH$_3$) |
| 2.95 | (3H, d, NCH$_3$) |
| 3.00 | (3H, s, CONCH$_3$) |
| 3.77~4.40 | (4H, m, methylene) |

EXAMPLE 20

Synthesis of methyl N-[[[[[(5,5-dimethyl-2-thioxo-1,3,2-dioxaphosphorinan-2-yl)(ethyl)amino]sulfinyl]methylamino]carbonyl]oxy]ethanimidothioate.

Methyl N-[[[[[(5,5-dimethyl-2-thioxo-1,3,2-dioxaphosphorinan-2-yl)(ethyl)amino]sulfinyl]methylamino]carbonyl]oxy]ethanimidothioate was prepared by the procedure employed in Example 9, by reacting methyl N-[[(methylamino)carbonyl]oxy]ethanimidothioate (2.43 g, 0.015 mole), thionyl chloride (1.79 g, 0.015 mole), and 5,5-dimethyl-2-ethylamino-2-thioxo-1,3,2-dioxaphosphorinan (3.14 g, 0.015 mole) in pyridine (10 ml). Recrystallization from chloroform-hexane afforded 2.2 g of needles of the formula below, mp 136~138°.

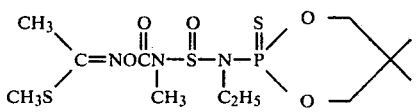

Analysis calculated for $C_{12}H_{24}N_3O_5S_3P$; carbon, 34.52%; hydrogen, 5.79%. Found: carbon, 34.84%; hydrogen, 6.11%.

The NMR spectrum (CDCl$_3$-TMS) of the compound showed the following absorptions:

| δ | |
|---|---|
| 0.97 | (3H, s, —C(CH$_3$)$_2$—) |
| 1.21 | (3H, s, —C(CH$_3$)$_2$—) |
| 1.23 | (3H, t, —NCH$_2$CH$_3$) |
| 2.27 | (3H, s, CH$_3$) |
| 2.38 | (3H, s, SCH$_3$) |
| 2.97 | (3H, s, CONCH$_3$) |
| 3.40–4.40 | (6H, m, O—CH$_2$/O—CH$_2$ and —NCH$_2$CH$_3$) |

EXAMPLE 21

Synthesis of methyl 2-(dimethylamino)-N-[[[[[(diethoxyphosphinothioyl)methylamino]sulfinyl]methylamino]carbonyl]oxy]-2-oxoethanimidothioate To a solution of methyl 2-(dimethylamino)-N-[[(methylamino)carbonyl]oxy]-2-oxoethanimidothioate (3.29 g, 0.015 mole) in dry pyridine 15 ml was added at one time thionyl chloride (1.79 g, 0.015 mole) at −30°. The mixture was allowed to come to room temperature and then stirred for 15 minutes. The mixture was cooled to 0° and O,O-diethyl methylphosphoramidothioate (2.75 g, 0.01 mole) was added. The mixture was allowed to come to room temperature for 1 hour, poured into ice water and extracted with benzene. The benzene solution was washed with water 4 times and then dried over anhydrous sodium sulfate. The benzene was removed under reduced pressure to give a crude product of the formula below.

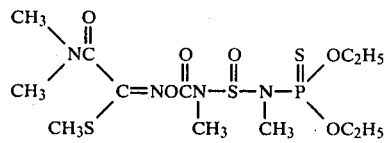

The product was purified by silica gel chromatography using benzene-acetonitrile (5:1) as an eluent, to yield 3.7 g. $n_D^{24}$: 1.5270.

The NMR spectrum (CDCl$_3$-TMS) of the compound showed the following absorptions:

| δ | |
|---|---|
| 1.30 | (6H, t, OCH$_2$CH$_3$) |
| 2.30 | (3H, s, SCH$_3$) |
| 2.78 | (3H, d, NCH$_3$) |
| 2.97 | (3H, s, CONCH$_3$) |
| 3.00 | (3H, s, N[CH$_3$]$_2$) |
| 3.07 | (3H, s, N[CH$_3$]$_2$) |
| 3.90~3.27 | (4H, m, OCH$_2$CH$_3$) |

EXAMPLE 22

Synthesis of methyl 2-(dimethylamino)-N-[[[[[(diethoxyphosphinothioyl)ethylamino]sulfinyl]methylamino]carbonyl]oxy]-2-oxoethanimidothioate Methyl 2-(dimethylamino)-N-[[[[[(diethoxyphosphinothioyl)ethylamino]sulfinyl]methylamino]carbonyl]oxy]-2-oxo-ethanimidothioate was prepared by the procedure employed in Example 21, by reacting methyl 2-(dimethylamino)-N-[[(methylamino)carbonyl]oxy]-2-oxoethanimidothioate (3.29 g,. 0.015 mole), thionyl chloride (1.79 g, 0.015 mole), and O,O-diethyl ethylphosphoramidothioate (2.96 g, 0.015 mole) in pyridine (10 ml). Column chromatography afforded 3.5 g of an oil of the formula below, $n_D^{24}$ 1.5230.

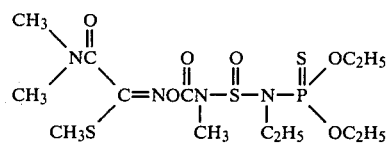

The NMR spectrum (CDCl$_3$-TMS) of the compound showed the following absorptions:

| δ | |
|---|---|
| 1.20 | (3H, t, NCH$_2$CH$_3$) |
| 1.32 | (6H, t, OCH$_2$CH$_3$) |
| 2.27 | (3H, s, SCH$_3$) |
| 2.91 | (3H, s, CONCH$_3$) |
| 3.00 | (3H, s, N[CH$_3$]$_2$) |
| 3.08 | (3H, s, N[CH$_3$]$_2$) |
| 3.23~3.63 | (2H, m, NCH$_2$CH$_3$) |
| 3.90~4.23 | (4H, m, OCH$_2$CH$_3$) |

EXAMPLE 23

Synthesis of methyl 2-(dimethylamino)-N-[[[[[(diethoxyphosphinothioyl)isopropylamino]sulfinyl]methylamino]carbonyl]oxy]-2-oxoethanimidothioate Methyl 2-(dimethylamino)-N-[[[[[(diethoxyphosphinothioyl)isopropylamino]sulfinyl]methylamino]carbonyl]oxy]-2-oxoethanimidothioate was prepared by the procedure employed in Example 21, by reacting methyl 2-(dimethylamino)-N-[[(methylamino)carbonyl]oxy]-2-oxoethanimidothioate (3.29 g, 0.015 mole), thionyl chloride (1.79 g, 0.015 mole), and O,O-diethyl isopropylphosphoramidothioate (3.17 g, 0.015 mole) in pyridine (10 ml). Column chromatography afforded 2.6 g of an oil of the formula below, $n_D^{24}$ 1.5211

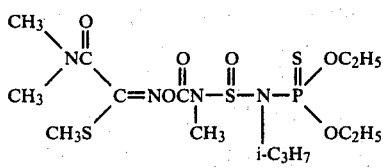

The NMR spectrum (CDCl₃-TMS) of the compound showed the following absorptions:

| δ | |
|---|---|
| 1.30 | (3H, t, —OCH₂CH₃) |
| 1.32 | (3H, t, —OCH₂CH₃) |
| 1.39 | (3H, d, —CH[CH₃]₂) |
| 1.43 | (3H, d, —CH[CH₃]₂) |
| 2.30 | (3H, s, SCH₃) |
| 2.93 | (3H, s, CONCH₃) |
| 3.03 | (3H, s, N[CH₃]₂) |
| 3.10 | (3H, s, N[CH₃]₂) |

EXAMPLE 24

Synthesis of methyl 2-(dimethylamino)-N-[[[[[(diethoxyphosphinothioyl)cyclopentylamino]sulfinyl]methylamino]carbonyl]-oxy]-2-oxoethanimidothioate Methyl 2-(dimethylamino)-N-[[[[[(diethoxyphosphinothioyl)cyclopentylamino]sulfinyl]methylamino]carbonyl]oxy]-2-oxoethanimidothioate was prepared by the procedure employed in Example 21, by reacting methyl 2-(dimethylamino)-N-[[(methylamino)carbonyl]oxy]-2-oxoethanimidothioate (3.29 g, 0.015 mole), thionyl chloride (1.79 g, 0.015 mole), and O,O-diethyl cyclopentylphosphoramidothioate (3.56 g, 0.015 mole) in pyridine (10 ml). Column chromatography afforded 2.5 g of an oil of the formula below, n_D²⁴: 1.5322.

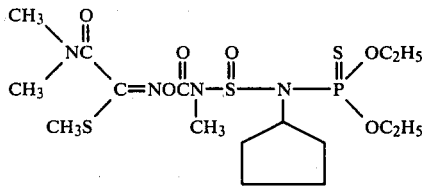

The NMR spectrum (CDCl₃-TMS) of the compound showed the following absorptions:

| δ | |
|---|---|
| 1.28 | (3H, t, OCH₂CH₃) |
| 1.30 | (3H, t, OCH₂CH₃) |
| 1.30~2.30 | (8H, m, cyclopentyl) |
| 2.30 | (3H, s, SCH₃) |
| 2.97 | (3H, s, CONCH₃) |
| 3.00 | (3H, s, N[CH₃]₂) |
| 3.60~4.30 | (8H, m, OCH₂CH₃, and methine proton) |

EXAMPLE 25

Synthesis of methyl 2-(dimethylamino)-N-[[[[[(5,5-dimethyl-2-thioxo-1,3,2-dioxaphosphorinan-2-yl)(methyl)amino]sulfinyl]methylamino]carbonyl]oxy]-2-oxoethanimidothioate Methyl 2-(dimethylamino)-N-[[[[[(5,5-dimethyl-2-thioxo-1,3,2-dioxaphosphorinan-2-yl)(methyl)amino]sulfinyl]methylamino]carbonyl]oxy]-2-oxoethanimidothioate was prepared by the procedure employed in Example 21, by reacting methyl 2-(dimethylamino)-N-[[(methylamino)carbonyl]oxy]-2-oxoethanimidothioate (3.29 g, 0.015 mole), thionyl chloride (1.79 g, 0.015 mole), and 5,5-dimethyl-2-methylamino-2-thioxo-1,3,2-dioxaphosphorinan (2.93 g, 0.015 mole) in pyridine (10 ml). Column chromatography afforded 4.5 g of an oil of the formula below, n_D²⁴: 1.5365.

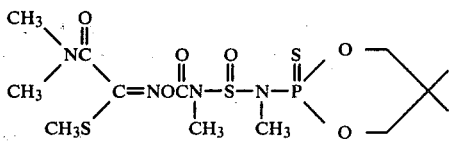

The NMR spectrum (CDCl₃-TMS) of the compound showed the following absorptions:

| δ | |
|---|---|
| 0.97 | (3H, s, —C(CH₃)(CH₃)—) |
| 1.18 | (3H, s, —C(CH₃)(CH₃)—) |
| 2.30 | (3H, s, SCH₃) |
| 2.90 | (3H, d, NCH₃) |
| 2.97 | (3H, s, CONCH₃) |
| 3.00 | (3H, s, N[CH₃]₂) |
| 3.07 | (3H, s, N[CH₃]₂) |
| 3.70–4.67 | (4H, m, O—CH₂ / O—CH₂ ring) |

The following are additional examples of the sulfinyl carbamate compounds of the invention:

2,3-Dihydro-2,2-dimethyl-7-benzofuranyl[[(dimethoxyphosphinyl)methylamino]sulfinyl]methylcarbamate,
2,3-Dihydro-2,2-dimethyl-7-benzofuranyl[[(dimethoxyphosphinyl)ethylamino]sulfinyl]methylcarbamate,
2,3-Dihydro-2,2-dimethyl-7-benzofuranyl[[(dimethoxyphosphinyl)propylamino]sulfinyl]methylcarbamate,
2,3-Dihydro-2,2-dimethyl-7-benzofuranyl[[(dimethoxyphosphinothioyl)methylamino]sulfinyl]methylcarbamate,
2,3-Dihydro-2,2-dimethyl-7-benzofuranyl[[(dimethoxyphosphinothioyl)ethylamino]sulfinyl]methylcarbamate,
2,3-Dihydro-2,2-dimethyl-7-benzofuranyl[[(dimethoxyphosphinothioyl)propylamino]sulfinyl]methylcarbamate,
2,3-Dihydro-2,2-dimethyl-7-benzofuranyl[[(dimethoxyphosphinothioyl)isopropylamino]sulfinyl]methylcarbamate,
2,3-Dihydro-2,2-dimethyl-7-benzofuranyl[[(dimethoxyphosphinothioyl)cyclohexylamino]sulfinyl]methylcarbamate,
2,3-Dihydro-2,2-dimethyl-7-benzofuranyl[[(diethoxyphosphinothioyl)ethylamino]sulfinyl]methylcarbamate, 2,3-Dihydro-2,2-dimethyl-7-benzofuranyl[[diethoxyphosphinothioyl)isopropylamino]sulfinyl]methylcarbamate,
2,3-Dihydro-2,2-dimethyl-7-benzofuranyl[[diethoxyphosphinothioyl)butylamino]sulfinyl]methylcarbamate,
2,3-Dihydro-2,2-dimethyl-7-benzofuranyl[[(diethoxyphosphinothioyl)isobutylamino]sulfinyl]methylcarbamate,
2,3-Dihydro-2,2-dimethyl-7-benzofuranyl[[(diethoxyphosphinothioyl)sec-butylamino]sulfinyl]methylcarbamate,
2,3-Dihydro-2,2-dimethyl-7-benzofuranyl[[(diethoxyphosphinothioyl)cyclohexylamino]sulfinyl]methylcarbamate,
2,3-Dihydro-2,2-dimethyl-7-benzofuranyl[[2-thioxo-1,3,2-dioxaphosphorinan-2-yl)methylamino]sulfinyl]methylcarbamate,
2,3-Dihydro-2,2-dimethyl-7-benzofuranyl[[(2-thioxo-1,3,2-dioxaphosphorinan-2-yl)ethylamino]sulfinyl]methylcarbamate,
2,3-Dihydro-2,2-dimethyl-7-benzofuranyl[[(2-thioxo-1,3,2-dioxaphosphorinan-2-yl)propylamino]sulfinyl]methylcarbamate,
2,3-Dihydro-2,2-dimethyl-7-benzofuranyl[[(5,5-dimethyl-2-thioxo-1,3,2-dioxaphosphorinan-2-yl)ethylamino]sulfinyl]methylcarbamate,
2,3-Dihydro-2,2-dimethyl-7-benzofuranyl([[5,5-dimethyl-2-thioxo-1,3,2-dioxaphosphorinan-2-yl)propylamino]sulfinyl]methylcarbamate,
2,3-Dihydro-2,2-dimethyl-7-benzofuranyl([[5,5-dimethyl-2-thioxo-1,3,2-dioxaphosphorinan-2-yl)isopropylamino]sulfinyl]methylcarbamate,
2,3-Dihydro-2,2-dimethyl-7-benzofuranyl[[5,5-dimethyl-2-thioxo-1,3,2-dioxaphosphorinan-2-yl)butylamino]sulfinyl]methylcarbamate,
2,3-Dihydro-2,2-dimethyl-7-benzofuranyl[[(5,5-dimethyl-2-thioxo-1,3,2-dioxaphosphorinan-2-yl)cyclohexylamino]sulfinyl]methylcarbamate,
2,3-Dihydro-2,2-dimethyl-7-benzofuranyl[[(5,5-dimethyl-1,3,2-dioxaphosphorinan-2-yl)methylamino]sulfinyl]methylcarbamate,
Methyl-N-[[[[[(dimethoxyphosphinothioyl)propylamino]sulfinyl]methylamino]carbonyl]oxy]ethanimidothioate,
Methyl-N-([[[[(dimethoxyphosphinothioyl)isopropylamino]sulfinyl]methylamino]carbonyl]oxy]ethanimidothioate,
Methyl-N-[[[[[(dimethoxyphosphinothioyl)cyclohexylamino]sulfinyl]methylamino]carbonyl]oxy]ethanimidothioate,
Methyl-N-[[[[[(5,5-dimethyl-2-thioxo-1,3,2-dioxaphosphorinan-2-yl)(propyl)amino]sulfinyl]methylamino]carbonyl]oxy]ethanimidothioate,
Methyl N-[[[[[(5,5-dimethyl-2-thioxo-1,3,2-dioxaphosphorinan-2-yl)(hexyl)amino]sulfinyl]methylamino]carbonyl]oxy]ethanimidothioate,
Methyl 2-(dimethylamino)-N-[[[[[(dimethoxyphosphinothioyl)methylamino]sulfinyl]methylamino]carbonyl]oxy]-2-oxoethanimidothioate,
Methyl 2-(dimethylamino)-N-[[[[[(dimethoxyphosphinothioyl)ethylamino]sulfinyl]methylamino]carbonyl]oxy]-2-oxoethanimidothioate,
Methyl 2-(dimethylamino)-N-[[[[[(dimethoxyphosphinothioyl)propylamino]sulfinyl]methylamino]carbonyl]oxy]-2-oxoethanimidothioate,
Methyl 2-(dimethylamino)-N-[[[[[(diethoxyphosphinothioyl)propylamino]sulfinyl]methylamino]carbonyl]oxy]-2-oxoethanimidothioate,
Methyl 2-(dimethylamino)-N-[[[[[(5,5-dimethyl-2-thioxo-1,3,2-dioxaphosphorinan-2-yl)(ethyl)amino]sulfinyl]methylamino]carbonyl]oxy]-2-oxoethanimidothioate,
Methyl 2-(dimethylamino)-N-[[[[[(5,5-dimethyl-2-thioxo-1,3,2-dioxaphosphorinan-2-yl)(propyl)amino]sulfinyl]methylamino]carbonyl]oxy-2-oxoethanimidothioate,
Methyl 2-(dimethylamino)-N-[[[[[(5,5-dimethyl-2-thioxo-1,3,2-dioxaphosphorinan-2-yl)(isopropyl)amino]sulfinyl]methylamino]carbonyl]oxy-2-oxoethanimidothioate and
Methyl 2-(dimethylamino)-N-[[[[[(5,5-dimethyl-2-thioxo-1,3,2-dioxaphosphorninan-2-yl)(hexyl)amino]sulfinyl]methylamino]carbonyl]oxy]-2-oxoethanimidothioate.

The insecticidal sulfinylcarbamates of the invention may be forumulated with the usual carriers, including additives and extenders used in the preparation of the insecticidal compositions. Thus, the toxicants of this invention, like most insecticidal agents, are generally not applied full strength, but are incorporated with the adjuvants and carriers normally employed for facilitating the dispersion of active ingredients, recognizing the accepted fact that the formulation and mode of application of a toxicant may affect the activity of the material.

The present compounds may be made into liquid concentrates by solution or emulsification in suitable liquids such as organic solvents, and into solid concentrates by admixing with talc, clays and other known solid carriers used in the insecticide art. These concentrates are compositions containing about 5–95% toxicant and the rest inert material which includes dispersing agents, emulsifying agents, and wetting agents. The concentrates are diluted for practical application with water or other liquid for liquid sprays or with additional solid carrier for application as a dust or granular formulation.

The concentration of the toxicant in the dilution generally used for application is normally in the range of about 2% to about 0.001%. Many variations of spraying and dusting compositions in the art may be used, by substituting a compound of this invention into the compositions known or apparent to the art.

The present compounds may also be made into compositions which may be applied without further dilution, for example dusts, powders and granules. These ready to use formulations generally contain from about 0.1% to 50% of the toxicant, preferably about 1.0% to about 45%.

The insecticidal compositions may be formulated and applied with other active ingredients, including other insecticides, nematicides, acaricides, fungicides, plant regulators, fertilizers, etc. In applying the chemicals, it is obvious that an effective amount and concentration of the carbamate ester compounds of the invention should be employed.

BIOLOGICAL ACTIVITY

Representative carbamate esters of the invention were tested for insecticidal activity against house flies, *Musca domestica*. Stock 1% concentrated solutions of each of the test compounds were made in acetone, and such solutions diluted with acetone to a concentration of 0.001–0.1%. House flies were treated topically on the notum by 1 μl of each of the diluted acetone solutions and percent mortality was counted 24 hours after application. The insects were held at a constant temperature of 60° F. Results are given in μg/g.

Mammalian toxicity was determined against Swiss white mice. The test compound was applied orally using corn oil as the carrier. Results are given as $LD_{50}$ in mg of compound per kg body weight.

The test data for a number of carbamates of the invention are summarized in Table 1. In that table the term "$LD_{50}$" represents the dose needed to kill 50% of the test animals. In interpreting the values in Table 1 below, the lower the value for $LD_{50}$ for house flies, the greater the insecticidal potency or toxicity of that particular compound. On the other hand, the higher the value of $LD_{50}$ for mice, the lower the mammalian toxicity or the greater is the mammalian safety of such compound.

Referring now to Table 1, the parent carbamate ester material of the compounds of Examples 1–8, carbofuran, (2,3-dihydro-2,2-dimethyl-7-benzofuranyl methylcarbamate) is known to have an $LD_{50}$ for house flies of about 6.5 and an $LD_{50}$ for mice in the range of about 2 to about 8 mg/kg. In Table 1 it is shown that while the corresponding compounds of this invention have a relatively comparable $LD_{50}$ for house flies (insecticidal activity), ranging from 3 to 19 μg/g, all have much higher $LD_{50}$ values for mice, ranging from 60 to 140, evidencing substantially lower mammalian toxicity and thus a higher margin of safety.

Similarly, the other compounds of this invention retain insecticidal activity relatively comparable to that of the carbamate ester on which they are based but have substantially reduced mammalian toxicity and thus substantially greater mammalian safety.

TABLE

| Compound of Example | House flies $LD_{50}$ (μg/g) | Mice $LD_{50}$ (oral) (mg/kg) |
|---|---|---|
| 1 | 14 | 65 |
| 2 | 16 | 60 |
| 3 | 19 | 140 |
| 4 | — | >1000 |
| 5 | 3 | 70 |
| 6 | — | 105 |
| 7 | 19 | — |
| 8 | — | 100 |
| 9 | 24 | 120 |
| 10 | 14 | — |
| 11 | 12 | 130 |
| 12 | 13 | — |
| 13 | 8 | 120 |
| 14 | 11 | — |
| 15 | 10 | — |
| 16 | 12 | — |
| 17 | 23 | 250 |
| 18 | 18 | — |
| 19 | 58 | 200 |
| 20 | 120 | — |
| 21 | 15 | 23 |
| 22 | 18 | — |
| 23 | 10 | 22 |
| 24 | 16 | — |
| 25 | 150 | 25 |

Although the foregoing invention has been described in some detail by way of illustration and example, changes in form and the substitution of equivalents are contemplated as circumstances may suggest or render expedient; and although specific terms have been employed herein, they are intended in a descriptive sense and not for purposes of limitation, the scope of the invention being delineated in the following claims.

What is claimed:

1. A compound of the formula

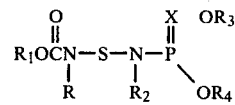

wherein R is alkyl of 1 to 4 carbon atoms; $R_1$ is a heterocyclic group of the formula

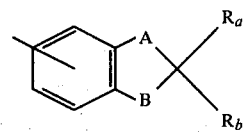

in which $R_a$ and $R_b$ are hydrogen or alkyl of 1 to 4 carbon atoms, A and B are each oxygen, or one and A and B is methylene and the other is oxygen or sulfur, wherein $R_1$ is attached at the 4 or 7 position; or an imino group of the formula

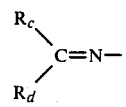

wherein $R_c$ is hydrogen, a dialkylaminocarbonyl or alkyl of 1 to 4 carbon atoms and $R_d$ is alkylthio or alkylthioalkyl and wherein the alkyl groups are the same or different and have 1 to 4 carbon atoms;

$R_2$ is alkyl of 1 to 12 carbon atoms; or cycloalkyl of 3 to 6 carbon atoms;

X is oxygen or sulfur; and $R_3$ and $R_4$ are the same or different and are alkyl of 1 to 6 carbon atoms; or together constitute the carbons necessary to complete a 5 to 6 membered ring system which is either unsubstituted or substituted by 1 or 2 methyl groups at the fifth position.

2. The compound of claim 1 wherein R is methyl.

3. The compound of claim 1 wherein $R_1$ is a heterocyclic group of the formula

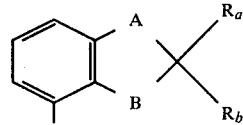

in which $R_a$ and $R_b$ are hydrogen or alkyl of 1 to 4 carbon atoms, A and B are oxygen or one of A and B is methylene and the other is oxygen or sulfur.

4. The compound of claim 1 wherein $R_1$ is an imino group of the formula

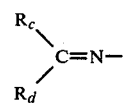

5. The compound of claim 3 wherein R is methyl.

6. The compound of claim 4 wherein R is methyl.

7. The compound of claim 5 wherein $R_1$ is a 2,3-dihydro-2,2-dimethyl-7-benzofuranyl group.

8. The compound of claim 6 wherein $R_1$ is selected from the formula $$CH_3\diagdown_{C=N-} \quad or \quad CH_3\diagdown_{NC}\overset{O}{\overset{\|}{\diagdown}}_{C=N-}$$
$$CH_3S\diagup \qquad\qquad CH_3\diagup \quad CH_3S\diagup$$

9. The compound of claim 5 wherein X is sulfur.

10. The compound of claim 6 wherein X is sulfur.

11. The compound of claim 7 wherein both $R_3$ and $R_4$ are methyl or ethyl.

12. The compound of claim 8 wherein both $R_3$ and $R_4$ are methyl or ethyl.

13. The compound of claim 9 wherein $R_3$ and $R_4$ together are $$-CH_2-\underset{\underset{CH_3}{|}}{\overset{\overset{CH_3}{|}}{C}}-CH_2-.$$

14. The compound of claim 10 wherein $R_3$ and $R_4$ together are $$-CH_2-\underset{\underset{CH_3}{|}}{\overset{\overset{CH_3}{|}}{C}}-CH_2-.$$

15. The compound of claim 1 which is 2,3-dihydro-2,2-dimethyl-7-benzofuranyl[[(diethoxyphosphinothioyl)methylamino]sulfinyl]methylcarbamate.

16. The compound of claim 1 which is 2,3-dihydro-2,2-dimethyl-7-benzofuranyl[[(diethoxyphosphinothioyl)hexylamino]sulfinyl]methylcarbamate.

17. The compound of claim 1 which is methyl N-[[[[[(dimethoxyphosphinothioyl)methylamino]sulfinyl]methylamino]carbonyl]oxy]ethanimidothioate.

18. The compound of claim 1 which is methyl N-[[[[[(diethoxyphosphinothioyl)ethylamino]sulfinyl]methylamino]carbonyl]oxy]ethanimidothioate.

19. The compound of claim 1 which is methyl N-[[[[[(diethoxyphosphinothioyl)hexylamino]sulfinyl]methylamino]carbonyl]oxy]ethanimidothioate.

20. The compound of claim 1 which is methyl N-[[[[[(diethoxyphinothioyl)isopropylamino]sulfinyl]methylamino]carbonyl]oxy]ethanimidothioate.

21. The compound of claim 1 which is 2,3-dihydro-2,2-dimethyl-7-benzofuranyl[[(5,5-dimethyl-2-thioxo-1,3,2-dioxaphosphorinan-2-yl)methylamino]sulfinyl]methylcarbamate.

22. The compound of claim 1 which is methyl N-[[[[[(5,5-dimethyl-2-thioxo-1,3,2-dioxaphosphorinan-2-yl)(methyl)amino]sulfinyl]methylamino]carbonyl]oxy]ethanimidothioate.

23. The method of controlling insects which comprises applying to sites of insectile infestation an amount of a compound as defined in claim 1, said amount being effective for said control.

* * * * *

UNITED STATES PATENT AND TRADEMARK OFFICE
CERTIFICATE OF CORRECTION

PATENT NO. : 4,410,518
DATED : October 18, 1983
INVENTOR(S) : T. Fukuto et al

It is certified that error appears in the above-identified patent and that said Letters Patent are hereby corrected as shown below:

Column 5, line 19, "(14H, m, $OCH_22CH_3$ and hexyl)" should be
--(14H, m, $OC\underline{H}_22CH_3$ and hexyl)--.

Column 5, line 22, "(2H, m, $NCH_2$)" should be --(2H, m, $NC\underline{H}_2$)--.

Column 5, line 23, "(4H, m, $OCH_2CH_3$)" should be
--(4H, m, $OC\underline{H}_2CH_3$)--.

Column 5, line 54, "(26H, m, $OCH_2CH_3$, and" should be
--(26H, m, $OCH_2C\underline{H}_3$, and--.

Column 5, line 58, "(2H, quintet $NCH_2$)" should be
--(2H, quintet $NC\underline{H}_2$)--.

Column 5, line 59, "(4H, m, $OCH_2CH_3$)" should be
--(4H, m, $OC\underline{H}_2CH_3$)--.

Column 8, line 4, "(4H, quintet $OCH_2CH_3$)" should be
--(4H, quintet $OC\underline{H}_2CH_3$)--.

Column 5, line 10, "n-$C_6H_{13}$" should be --$\underline{n}$-$C_6H_{13}$--.

Column 8, line 36, "(3H, t, $CH_2CH_2CH_3$)" should be
--(3H, t, $CH_2CH_2C\underline{H}_3$)--.

UNITED STATES PATENT AND TRADEMARK OFFICE
CERTIFICATE OF CORRECTION

PATENT NO. : 4,410,518

DATED : October 18, 1983

INVENTOR(S) : T. Fukuto et al

It is certified that error appears in the above-identified patent and that said Letters Patent are hereby corrected as shown below:

Column 8, line 37, "(3H, t, OCH$_2$CH$_3$)" should be --(3H, t, OCH$_2$C$\underline{H}$$_3$)--.

Column 8, line 38, "(3H, t, OCH$_2$CH$_3$)" should be --(3H, t, OC$\underline{H}$$_2$CH$_3$)--.

Column 8, line 40, "(2H, m, -CH$_2$CH$_2$CH$_3$)" should be --(2H, m, -CH$_2$C$\underline{H}$$_2$CH$_3$)--.

Column 8, line 42, "(2H, m, -CH$_2$CH$_2$CH$_3$)" should be --(2H, m, -C$\underline{H}$$_2$CH$_2$CH$_3$)--.

Column 8, line 43, "(4H, quintet, OCH$_2$CH$_3$)" should be --(4H, quintet, OC$\underline{H}$$_2$CH$_3$)--.

Column 9, line 46, "(3H, t, NCH$_2$CH$_3$)" should be --(3H, t, NCH$_2$C$\underline{H}$$_3$)--.

Column 9, line 50, "(2H, sextet, NCH$_2$CH$_3$)" should be --(2H, sextet, NC$\underline{H}$$_2$CH$_3$)--.

Column 9, line 51, "(6H, d, OCH$_3$)" should be --(6H, d, OC$\underline{H}$$_3$)--.

Column 10, line 15, "(6H, t, OCH$_2$CH$_3$)" should be --(6H, t, OCH$_2$C$\underline{H}$$_3$)--.

UNITED STATES PATENT AND TRADEMARK OFFICE
CERTIFICATE OF CORRECTION

PATENT NO. : 4,410,518
DATED : October 18, 1983
INVENTOR(S) : T. Fukuto et al

It is certified that error appears in the above-identified patent and that said Letters Patent are hereby corrected as shown below:

Column 10, line 19, "(4H, m, $OCH_2CH_3$)" should be
--(4H, m, $O\underline{CH}_2CH_3$)--.

Column 10, line 50, "(3H, t, $CH_2CH_3$)" should be
--(3H, t, $CH_2\underline{CH}_3$)--.

Column 10, line 51, "(6H, t, $OCH_2CH_3$)" should be
--(6H, t, $OCH_2\underline{CH}_3$)--.

Column 10, line 55, "(2H, sextet, $CH_2CH_3$)" should be
--(2H, sextet, $\underline{CH}_2CH_3$)--.

Column 10, line 56, "(4H, quintet, $OCH_2CH_3$)" should be
--(4H, quintet, $O\underline{CH}_2CH_3$)--.

Column 11, line 18, "(3H, t, -$CH_2CH_2CH_3$)" should be
--(3H, t, -$CH_2CH_2\underline{CH}_3$)--.

Column 11, line 19, "(6H, t, -$OCH_2CH_3$)" should be
--(6H, t, -$OCH_2\underline{CH}_3$)--.

Column 11, line 20, "(2H, m, -$CH_2CH_2CH_3$)" should be
--(2H, m, -$CH_2\underline{CH}_2CH_3$)--.

UNITED STATES PATENT AND TRADEMARK OFFICE
CERTIFICATE OF CORRECTION

PATENT NO. : 4,410,518

DATED : October 18, 1983

INVENTOR(S) : T. Fukuto et al

Page 4 of 7

It is certified that error appears in the above-identified patent and that said Letters Patent are hereby corrected as shown below:

Column 11, line 52, "(6H, m, $OCH_2CH_3$)" should be --(6H, m, $OC\underline{H}_2\underline{CH}_3$)--.

Column 11, line 53, "(6H, d, $[CH_3]_2CH$-)" should be --(6H, d, $[C\underline{H}_3]_2CH$-)--.

Column 11, line 57, "(5H, m, $OCH_2CH_3$" should be --(5H, m, $OC\underline{H}_2CH_3$--.

Column 11, line 58, "and $[CH_3]_2CH$)" should be --and $[CH_3]_2C\underline{H}$)--.

Column 12, line 18, "(3H, t, $CH[CH_3]CH_2CH_3$)" should be --(3H, t, $CH[CH_3]CH_2C\underline{H}_3$)--.

Column 12, line 20, "$CH[CH_3]CH_2CH_3$)" should be --$CH[CH_3]CH_2C\underline{H}_3$)--.

Column 12, line 21, "(2H, m, $CH[CH_3]CH_2CH_3$)" should be --(2H, m, $CH[CH_3]C\underline{H}_2CH_3$)--.

Column 12, line 25, "(5H, m, $OCH_2CH_3$" should be --(5H, m, $OC\underline{H}_2CH_3$--.

Column 12, line 26, "$CH[CH_3]CH_2CH_3$)" should be --$C\underline{H}[CH_3]CH_2CH_3$)--.

UNITED STATES PATENT AND TRADEMARK OFFICE
CERTIFICATE OF CORRECTION

PATENT NO. : 4,410,518
DATED : October 18, 1983
INVENTOR(S) : T. Fukuto et al

It is certified that error appears in the above-identified patent and that said Letters Patent are hereby corrected as shown below:

Column 12, line 56, "(3H, t, $OCH_2CH_3$)" should be --(3H, t, $OCH_2C\underline{H}_3$)--.

Column 12, line 57, "(3H, t, $OCH_2CH_3$)" should be --(3H, t, $OCH_2C\underline{H}_3$)--.

Column 12, line 62, "(5H, m, $OCH_2CH_3$, N-CH)" should be --(5H, m, $OC\underline{H}_2CH_3$, N-CH)--.

Column 13, line 22, "(3H, t, $OCH_2CH_3$)" should be --(3H, t, $OCH_2C\underline{H}_3$)--.

COlumn 13, line 23, "(3H, t, $OCH_2CH_3$)" should be --(3H, t, $OCH_2C\underline{H}_3$)--.

Column 13, line 28, "(2H, quintet, $NCH_2$)" should be --(2H, quintet, $NC\underline{H}_2$)--.

Column 13, line 29, "(4H, m, $OCH_2CH_3$)" should be --(4H, m, $OC\underline{H}_2CH_3$)--.

Column 13, line 63, "(3H, t, $OCH_2CH_3$)" should be --(3H, t, $OCH_2C\underline{H}_3$)--.

Column 13, line 64, "(3H, t, $OCH_2CH_3$)" should be --(3H, t, $OCH_2C\underline{H}_3$)--.

UNITED STATES PATENT AND TRADEMARK OFFICE
CERTIFICATE OF CORRECTION

PATENT NO. : 4,410,518
DATED : October 18, 1983
INVENTOR(S) : T. Fukuto et al

Page 6 of 7

It is certified that error appears in the above-identified patent and that said Letters Patent are hereby corrected as shown below:

Column 14, line 5, "(5H, m, OCH$_2$CH$_3$, N-CH<)" should be --(5H, m, OC$\underline{H}_2$CH$_3$, N-C$\underline{H}$<)--.

Column 15, line 26, "(3H, t, -NCH$_2$CH$_3$)" should be --(3H, t, -NCH$_2$C$\underline{H}_3$)--.

Column 16, line 4, "(6H, t, OCH$_2$CH$_3$)" should be --(6H, t, OCH$_2$C$\underline{H}_3$)--.

Column 16, line 10, "(4H, m, OCH$_2$CH$_3$)" should be --(4H, m, OC$\underline{H}_2$CH$_3$)--.

Column 16, line 43, "(3H, t, NCH$_2$CH$_3$)" should be --(3H, t, NCH$_2$C$\underline{H}_3$)--.

Column 16, line 44, "(6H, t, OCH$_2$CH$_3$)" should be --(6H, t, OCH$_2$C$\underline{H}_3$)--.

Column 16, line 49, "(2H, m, NCH$_2$CH$_3$)" should be --(2H, m, NC$\underline{H}_2$CH$_3$)--.

Column 16, line 50, "(4H, m, OCH$_2$CH$_3$)" should be --(4H, m, OC$\underline{H}_2$CH$_3$)--.

Column 17, line 14, "(3H, t, -OCH$_2$CH$_3$)" should be --(3H, t, -OCH$_2$C$\underline{H}_3$)--.

UNITED STATES PATENT AND TRADEMARK OFFICE
CERTIFICATE OF CORRECTION

PATENT NO. : 4,410,518
DATED : October 18, 1983
INVENTOR(S) : T. Fukuto et al

It is certified that error appears in the above-identified patent and that said Letters Patent are hereby corrected as shown below:

Column 17, line 15, "(3H, t, -OCH$_2$CH$_3$)" should be --(3H, t, -OCH$_2$C$\underline{H}_3$)--.

Column 17, line 16, "(3H, d, -CH[CH$_3$]$_2$)" should be --(3H, d, -C$\underline{H}$[CH$_3$]$_2$)--.

Column 17, line 51, "(3H, t, OCH$_2$CH$_3$)" should be --(3H, t, OCH$_2$C$\underline{H}_3$)--.

Column 17, line 52, "(3H, t, OCH$_2$CH$_3$)" should be --(3H, t, OCH$_2$C$\underline{H}_3$)--.

Column 17, line 57, "(8H, m, OCH$_2$CH$_3$" should be --(8H, m. OC$\underline{H}_2$CH$_3$--.

Signed and Sealed this

Fifth Day of February 1985

[SEAL]

Attest:

DONALD J. QUIGG

Attesting Officer       Acting Commissioner of Patents and Trademarks

United States Patent and Trademark Office

CERTIFICATE OF CORRECTION

PATENT NO. : 4,410,518
DATED : October 18, 1983
INVENTOR(S) : Tetsuo R. Fukuto et al.

It is certified that error appears in the above-identified patent and that said Letters Patent are hereby corrected as shown below:

Column 22, line 6, over "S" should be "$\overset{O}{\underset{\|}{}}$".

Column 22, line 7, "P" should be "$\overset{}{P}\diagup$".

Signed and Sealed this

Twenty-third Day of April 1985

[SEAL]

Attest:

DONALD J. QUIGG

Attesting Officer   Acting Commissioner of Patents and Trademarks